United States Patent
Kim et al.

(10) Patent No.: US 6,773,403 B2
(45) Date of Patent: Aug. 10, 2004

(54) ULTRASONIC APPARATUS AND METHOD FOR MEASURING THE VELOCITIES OF HUMAN TISSUES USING THE DOPPLER EFFECTS

(75) Inventors: Cheol An Kim, Seoul (KR); Sung Ho Kim, Seoul (KR)

(73) Assignee: Medison Co., Ltd., Hongchun-gun (KR)

( * ) Notice: Subject to any disclaimer, the term of this patent is extended or adjusted under 35 U.S.C. 154(b) by 0 days.

(21) Appl. No.: 10/413,205

(22) Filed: Apr. 15, 2003

(65) Prior Publication Data

US 2003/0199764 A1 Oct. 23, 2003

(30) Foreign Application Priority Data

Apr. 17, 2002 (KR) ................................ 10-2002-020839

(51) Int. Cl.⁷ ................................................. A61B 8/14
(52) U.S. Cl. ..................................................... 600/465
(58) Field of Search ................................. 600/437, 504, 600/455, 457, 465; 73/861.25, 625; 128/916

(56) References Cited

U.S. PATENT DOCUMENTS

| | | | | |
|---|---|---|---|---|
| 4,413,531 A | * | 11/1983 | Karplus et al. ........... | 73/861.25 |
| 4,556,067 A | * | 12/1985 | Hokanson et al. .......... | 600/457 |
| 5,107,841 A | * | 4/1992 | Sturgill ...................... | 600/455 |
| 5,582,176 A | * | 12/1996 | Swerling et al. ............ | 600/455 |
| 5,634,465 A | * | 6/1997 | Schmiesing et al. ........ | 600/454 |
| 6,036,643 A | * | 3/2000 | Criton et al. ................ | 600/454 |
| 6,447,455 B2 | * | 9/2002 | Bang et al. .................. | 600/454 |
| 6,530,890 B2 | * | 3/2003 | Bang et al. .................. | 600/504 |

FOREIGN PATENT DOCUMENTS

EP     0 481 691     4/1992

\* cited by examiner

Primary Examiner—Dennis W. Ruhl
Assistant Examiner—Ruby Jain
(74) Attorney, Agent, or Firm—Oblon, Spivak, McClelland, Maier & Neustadt, P.C.

(57) ABSTRACT

Apparatuses and methods for measuring a velocity component of tissue and blood flow within a human body may generate sample data by transmitting ultrasound signals to and sampling echo signals reflected from the human body, generate frequency distribution data containing the velocity component of tissue and blood flow, extract the frequency distribution data corresponding to the velocity component of tissue flow from the frequency distribution data, and display the extracted frequency distribution data. The apparatuses and methods may also input the frequency distribution data containing the velocity component of tissue and blood flow, eliminate a direct-current component of the frequency distribution data, extract the velocity component of blood flow from the frequency distribution data, determine a maximum value of the extracted velocity component of blood flow, decide a gain level, and multiply the frequency distribution data by the decided gain level.

8 Claims, 12 Drawing Sheets

ULTRASONIC APPARATUS AND METHOD FOR MEASURING THE VELOCITIES OF HUMAN TISSUES USING THE DOPPLER EFFECTS

FIELD OF THE INVENTION

The present invention relates generally to an ultrasound diagnostic system, and more particularly, to an ultrasonic apparatus and method for automatically measuring the velocities of tissues within the human body by using the Doppler effect.

BACKGROUND OF THE INVENTION

Ultrasound diagnostic systems using the Doppler effect are well known in the art and typically used for detection of the velocities of blood flows and tissues within the human body. These conventional ultrasound diagnostic systems determine the velocity of a target object, such as a red blood cell, by detecting a frequency or phase shift of echo signals, due to movement of the target object, which have been reflected from the target object based on transmitted ultrasound signals.

Referring to FIG. 1, the principle of measuring the velocity of blood flow and tissue by using ultrasound signals is explained. Transducer array 103 transmits ultrasound signals toward target object 101, and repeats sampling operations upon the echo signals reflected from target object 101, several times, e.g., 2N times. FIG. 1 exemplifies sampling done at the timing, $t=t_0$. As the target object moves, the phases of the signals sampled at the timing, $t=t_0$ change. From the degree of the phase changes, the velocity of target object 101, v, may be calculated according to Equation 1 below:

$$v = \frac{\Delta_\Theta \lambda_0}{2\pi T_{PRF}} \quad \text{(Eq. 1)}$$

where $T_{PRF}$ is an interval at which ultrasound signals are transmitted, i.e., the reciprocal of a pulse repetition frequency (PRF), $\lambda_0$ is a center frequency of the ultrasound signals being transmitted, and $\Delta_\Theta$ is a phase change.

As can be seen from Equation 1, the velocity of the target object is proportional to the phase change of the echo signals reflected from the target object. Since the frequency shift of the signal is proportional to the phase change, the velocity of the target object, v, is proportional to the frequency shift of the reflected echo signal. Therefore, measuring the frequency of the echo signals reflected from the target object provides the velocity of the target object.

Referring to FIG. 2, which shows a block diagram of a conventional ultrasound diagnostic apparatus for measuring the velocity of blood flow and human tissue, ultrasound diagnostic apparatus 200 comprises transducer array 103, pre-amplifier 104, time gain control (TGC) amplifier 105, analog-to-digital (A/D) converter 106, quadrature demodulator 107, digital signal processor 108, and display 109.

Transducer array 103 transmits ultrasound signals toward the target object and receives echo signals reflected from the target object. The echo signals are amplified by pre-amplifier 104. TGC amplifier 105 amplifies the pre-amplified signals from pre-amplifier 104 while varying gain to compensate for attenuation of the ultrasound signals as they propagate inside the human body. A/D converter 106 converts an output signal of TGC amplifier 105 from analog to digital and quadrature demodulator 107 demodulates the signal to be inputted to digital signal processor 108. Digital signal processor 108 detects the velocity of the target object based on 2N number of sampled data, which are obtained by repeating transmission of an ultrasound signal toward the target object, 2N times, and transmits the detected velocity to display 109.

The ultrasound signals transmitted by transducer array 103 are reflected from blood, tissues, muscles, and the like within the human body. In the case of blood, the ultrasound signals are reflected from a plurality of red blood cells, each of which has a different velocity. Since the sampled data being inputted to digital signal processor 108 contain a plurality of velocity components, digital signal processor 108 computes a velocity distribution spectrum of the sampled data and transmits the same to display 109. Display 109 then displays the velocity distribution spectrum of the sampled data thereon.

Referring to FIG. 3, which shows a block diagram of digital signal processor 108 shown in FIG. 2, digital signal processor 108 comprises clutter filtering part 301, fast Fourier transform (FFT) part 302, and post-processing part 303. Where ultrasound diagnostic apparatus 200 is used for measuring the velocity of blood flow, clutter filtering part 301 cuts off echo signals (so called clutters) reflected from tissues and/or muscles within the human body. These echo signals have low-band frequencies, since movement of tissue and muscle is slower than that of blood within the human body. Thus, clutter filtering part 301 employs a high-pass filter for computing velocity of blood flow.

If ultrasound diagnostic apparatus 200 is used for measuring the velocity of tissue within the human body, clutter filtering part 301 cuts off echo signals reflected from blood. In order to compute the velocity component of tissue, clutter filtering part 301 employs a low-pass filter instead of the high-pass filter to cut off the velocity components of blood flow.

FFT part 302 performs a Fourier transform on the 2N number of sampled data to create frequency distribution data containing 2N number of frequency components. This frequency distribution data corresponds to the velocity distribution data of the target object. Post-processing part 303 performs known signal processing on the frequency distribution data, such as log compression and base line shifting, in order to obtain improved image quality. The frequency distribution data, i.e., the velocity distribution data of the target object, outputted from digital signal processor 108, is displayed on display 109.

Referring to FIG. 4, which shows a graph of typical frequency distribution data, the X-axis represents frequency components and Y-axis represents the strength of the frequency components. The frequency distribution data may represent the strength of the frequency components or, alternatively, some other value, such as the square of the strength. A positive frequency and a negative frequency represent signal components reflected from target objects that move in opposite direction. That is, "positive" and "negative" denote relative direction of movement. As can be seen from FIG. 4, the strength of the negative frequency component tends to be larger than that of the positive frequency component. This means that the blood flows in a certain direction, such as away from transducer array 130.

Referring to FIGS. 5 and 6, employing a low-pass filter to cut off the velocity component of blood flow in order to measure the velocity component of tissue within the human body has some drawbacks. Calculating a cut-off frequency to precisely discriminate the velocity component of tissue from that of blood flow within the human body is very difficult. Changing the calculated cut-off frequency whenever the velocity of tissue is varied is also very difficult.

FIG. 5 shows a diagram of a conventional low-pass filtering scheme for isolating the velocity component of tissue within the human body. FIG. 6 shows a diagram of a method for designing a cut-off frequency that discriminates the velocity component of tissue from that of blood flow by using a conventional low-pass filtering scheme in a conventional ultrasound diagnostic apparatus.

Referring to FIG. 5, in a conventional ultrasound diagnostic apparatus, a low-pass filter 703 is designed on the basis of maximum frequency 701-1 in the frequency band representative of a velocity component of tissue 701, which appears in a low frequency band, in order to isolate the velocity component of tissue 701. Determining a cut-off frequency 704 for precisely discriminating the velocity component of tissue 701 from that of blood flow 702 is very important. However, the low-pass filtering scheme shown in FIG. 5 is difficult to adapt to an ultrasound diagnostic apparatus. Therefore, in a conventional ultrasound diagnostic apparatus, a low-pass filter designed as shown in FIG. 6 may be employed.

If the velocity component of tissue is limited to a predetermined velocity range, designing low-pass filter 703 on the basis of maximum frequency 701-1 of the velocity component of tissue 701 may be possible as shown in FIG. 5. However, since the velocity component of tissue 701 is actually different for each target object to be measured, determining a fixed cut-off frequency is very difficult.

As shown in FIG. 6, where the velocity component of tissue 701 is mixed with the velocity component of blood flow 702 having a low frequency component, designing a filter 703-1 with a low cut-off frequency results in the decrease in the velocity component of tissue 701, by as much as portion 701-2, while designing a filter 703-1 with a high cut-off frequency results in the high cut-off frequency containing the velocity component of blood flow 702. Thus, determining a cut-off frequency 704 for discriminating the velocity component of tissue 701 from the velocity component of blood flow 702 is very difficult in designing a filter.

Another drawback is that the velocity component of tissue within the human body may be erroneously calculated due to aliasing when a digital signal is processed. Referring to FIG. 7, the velocity component of tissue appears in a low frequency domain and the velocity component of blood flow appears in a high frequency domain. However, if the sampling frequency does not have a sufficiently high frequency, aliasing occurs such that the velocity component of blood flow 702 appears in the frequency domain of the velocity component of tissue 701. That is, where the velocity component of blood flow 702 appears within the velocity component of tissue 701 due to aliasing as shown in FIG. 7, the velocity component of tissue 701 will appear greater than its actual value. Thus, frequencies of the velocity component and power component are distorted whenever the velocity component of blood flow 702 is varied. This results in decreased reliability of the measured data.

Yet another drawback is that designing a filter with a cut-off frequency for discriminating the velocity component of tissue from that of blood flow by means of a finite-impulse-response (FIR) filter with a limited filter order is very difficult. Although designing a filter having a desired cut-off frequency by increasing the filter order is possible, delays corresponding to (the filter order (N)−1)/2 degrade the real-time processing capability. Also, in a gap filling mode, data sections (number of gaps+order of filter (N)−1) have to be filled, as will be described in detail with reference to FIGS. 8 to 12.

FIG. 8 shows a timing sequence in a typical brightness/Doppler (B/D) simultaneous mode. FIG. 9 shows a timing sequence in a gap filling mode. FIGS. 10A and 10B show views explaining the principle of spectrum gap filling. Here, B and D modes are used for obtaining a tomograph image and Doppler data, respectively. The B/D simultaneous mode is used for obtaining both a tomograph image and Doppler data.

In B/D simultaneous mode of a conventional ultrasound diagnostic apparatus employing a timing sequence shown in FIG. 8, raising a Doppler PRF to a sufficient level is difficult. For example, where blood flow within the heart is observed in a pulsed-wave (PW) Doppler simultaneous mode, aliasing greatly affects the Doppler spectrum so that analyzing the Doppler spectrum may be very difficult.

However, raising the Doppler PRF by two times is possible by implementing PW Doppler simultaneous mode with the timing sequence shown in FIG. 9 and approximately reconstructing the time gap in the PW Doppler simultaneous mode with image/audio artifacts from previous and next Doppler signals. In FIG. 9, a time interval required to obtain the B mode is associated with a minimum B mode frame rate that is synchronized with the PRF. Thus, the time interval acts as a time gap so that filling the time gap may increase the reliability of measured data.

Referring to FIGS. 10A and 10B, which show views explaining the principle of spectrum gap filling, in a conventional ultrasound diagnostic apparatus, a time gap, between $t_1$ to $t_2$, is filled by using linear interpolation.

Referring to FIG. 11, the number of data intervals, as much as (number of gaps+order of the filter (N)−1), must be filled. For example, where the number of gaps is 4 and the order of filter is 5, the number of filtered data is 8. This means that actually 8 gaps have to be filled despite the number of gap intervals being 4. If data in the gap interval is distorted data or zero, the filtered data may be distorted. Also, as the filter order is increased, the number of gaps to be filled is increased, so that discriminating the velocity component of tissue from the velocity component of blood flow is difficult. As a result, increasing the filter order is practically limited.

As will be described in detail with reference to FIG. 12, where the filter order is increased under such limitation, delays, (order of filter (N)−1)/2), occur so that real-time processing capability may be degraded. As shown in FIG. 12, if the filter order is 9, filtered data 1 can be outputted when data 1 to data 9 are inputted. In such a case, if the order of the filter is increased, the delay is increased as mentioned above. Therefore, the delay interval is increased as the filter order is increased so that real-time processing capability may be degraded.

Due to the afore-mentioned drawbacks, a conventional ultrasound diagnostic apparatus cannot effectively measure the velocity component of tissue within the human body by using a low-pass filter, which results in decreased reliability of the measured data.

SUMMARY OF THE INVENTION

Therefore, one objective of the present invention is to provide an ultrasound diagnostic apparatus and method for effectively measuring the velocity of tissue within the human body by using the Doppler effect.

Another objective is to provide an ultrasound diagnostic apparatus and method for measuring the velocity of tissue within the human body in real-time without using a low-pass filter.

Yet another objective is to provide an ultrasound diagnostic apparatus and method for effectively eliminating the velocity component of blood flow without using a low-pass filter, to thereby reliably measure the velocity of tissue within the human body.

In accordance with one aspect of the present invention, an ultrasound diagnostic apparatus is provided for measuring a velocity component of tissue and blood flow within a human body, comprising: a sample data generator for generating sample data by transmitting ultrasound signals to and sampling echo signals reflected from the human body; generating means for generating frequency distribution data containing the velocity component of tissue and blood flow by processing the sample data, wherein the frequency distribution data contains a plurality of frequency components, each of which has a power level; detecting means for extracting the frequency distribution data corresponding to the velocity component of tissue flow from the frequency distribution data, by using a maximum value of the velocity component of blood flow; and a display coupled to the detecting means for displaying the extracted frequency distribution data.

In accordance with another aspect of the present invention, a method is provided for measuring a velocity component of tissue and blood flow within a human body, comprising the steps of: generating sample data by transmitting ultrasound signals to and sampling echo signals reflected from the human body; generating frequency distribution data containing the velocity component of tissue and blood flow by processing the sample data, wherein the frequency distribution data contains a plurality of frequency components, each of which has a power level; extracting the frequency distribution data corresponding to the velocity component of tissue flow from the frequency distribution data, by using a maximum value of the velocity component of blood flow; and displaying the extracted frequency distribution data.

BRIEF DESCRIPTION OF DRAWINGS

The features of the present invention, which are believed to be novel, are set forth with particularity in the appended claims. The present invention, both as to its organization and manner of operation, together with further objects and advantages thereof, may best be understood with reference to the following description, taken in conjunction with the accompanying drawings.

DETAILED DESCRIPTION OF THE PRESENT INVENTION

Figure 1:
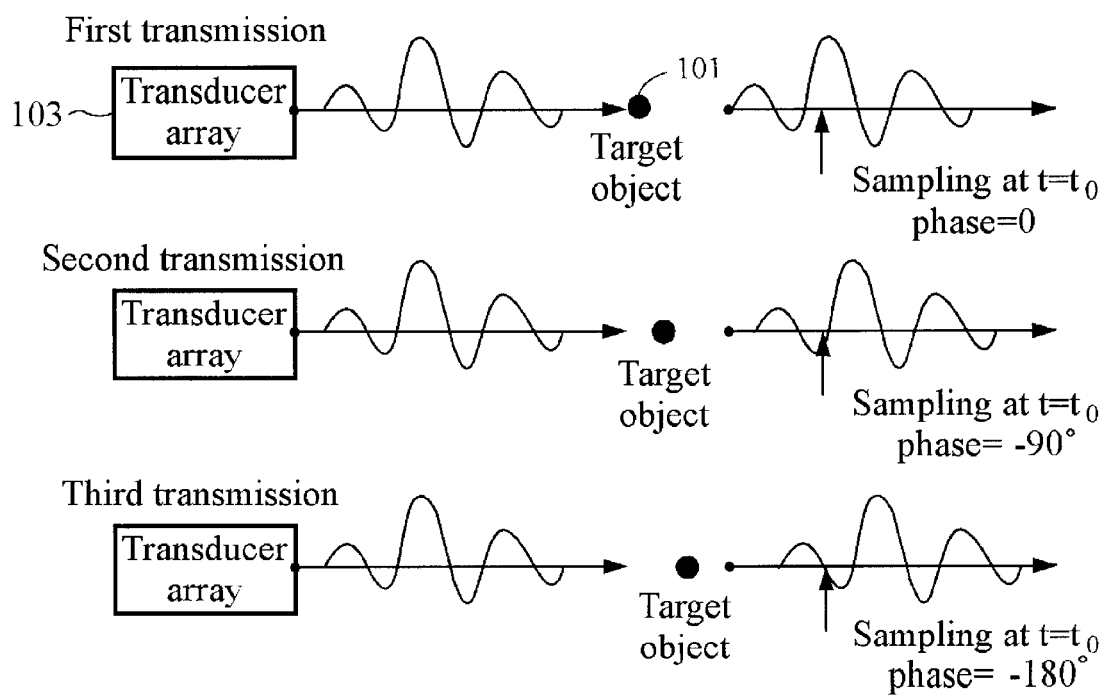
FIG. 1 shows a view explaining the principle of measuring the velocity of blood flow and tissue by using ultrasound signals.
Figure 2:
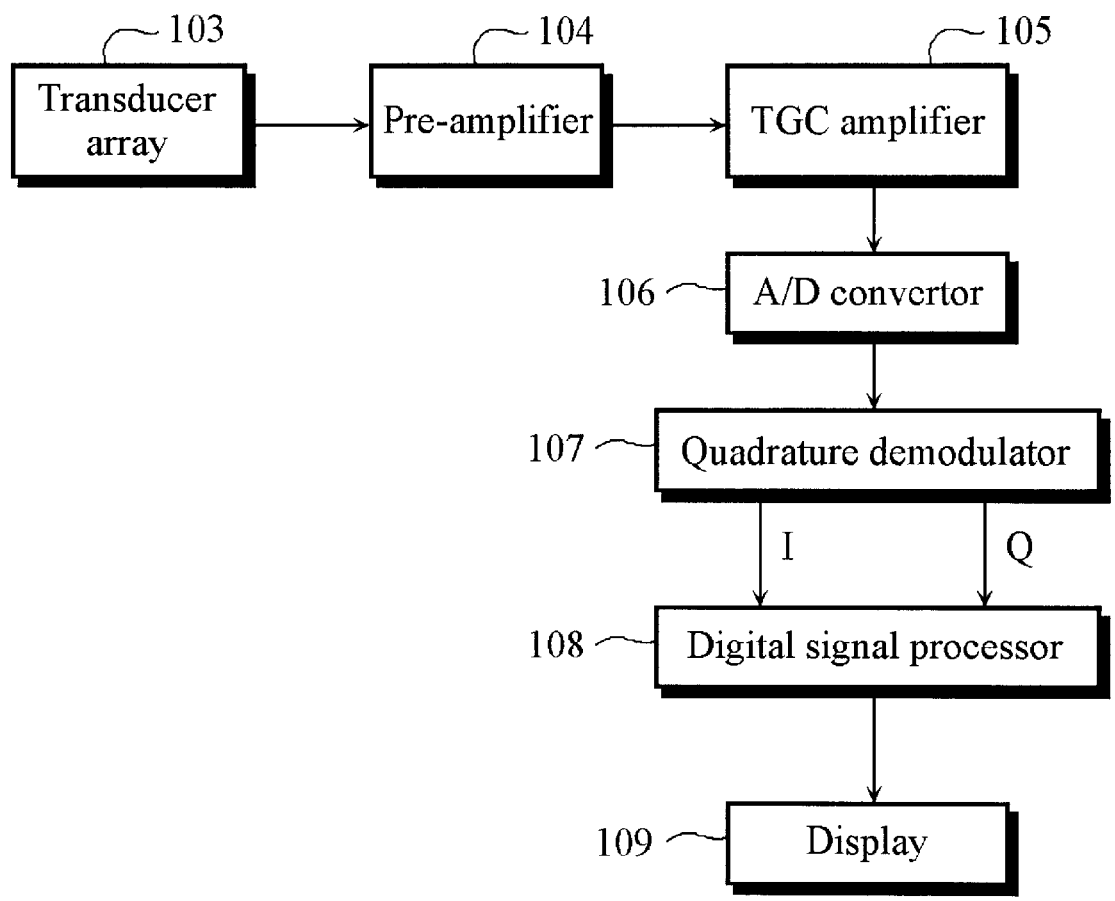
FIG. 2 shows a block diagram of a conventional ultrasound diagnostic apparatus for measuring the velocity of blood flow and tissue.
Figure 3:
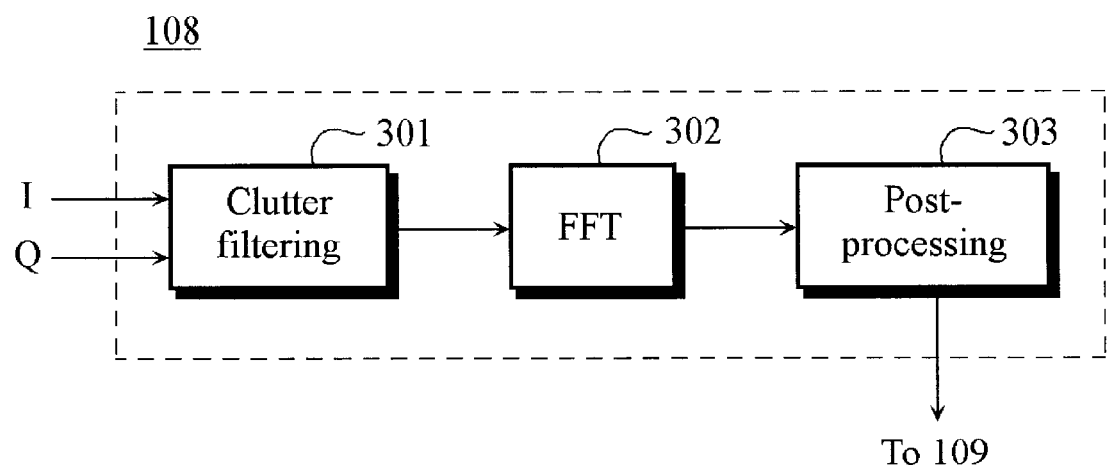
FIG. 3 shows a block diagram of the digital signal processor shown in FIG. 2.
Figure 4:
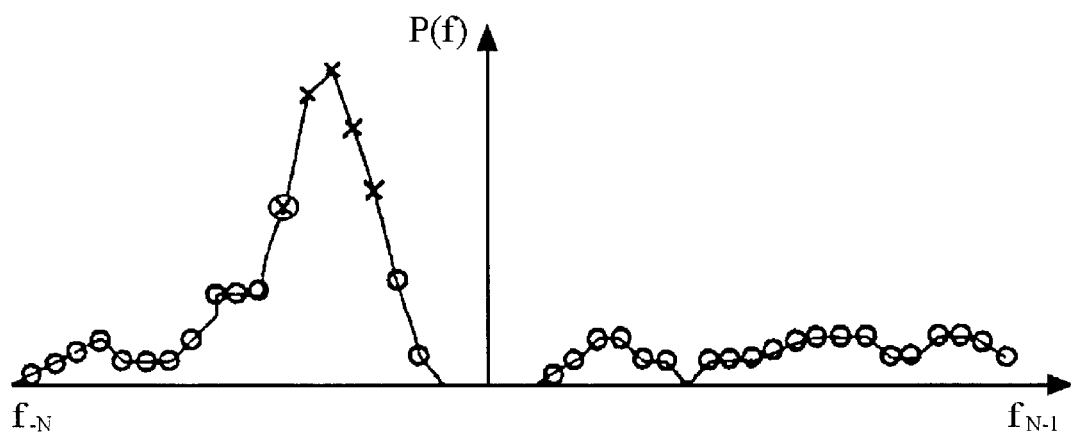
FIG. 4 shows typical frequency distribution data calculated from echo signals.
Figure 5:
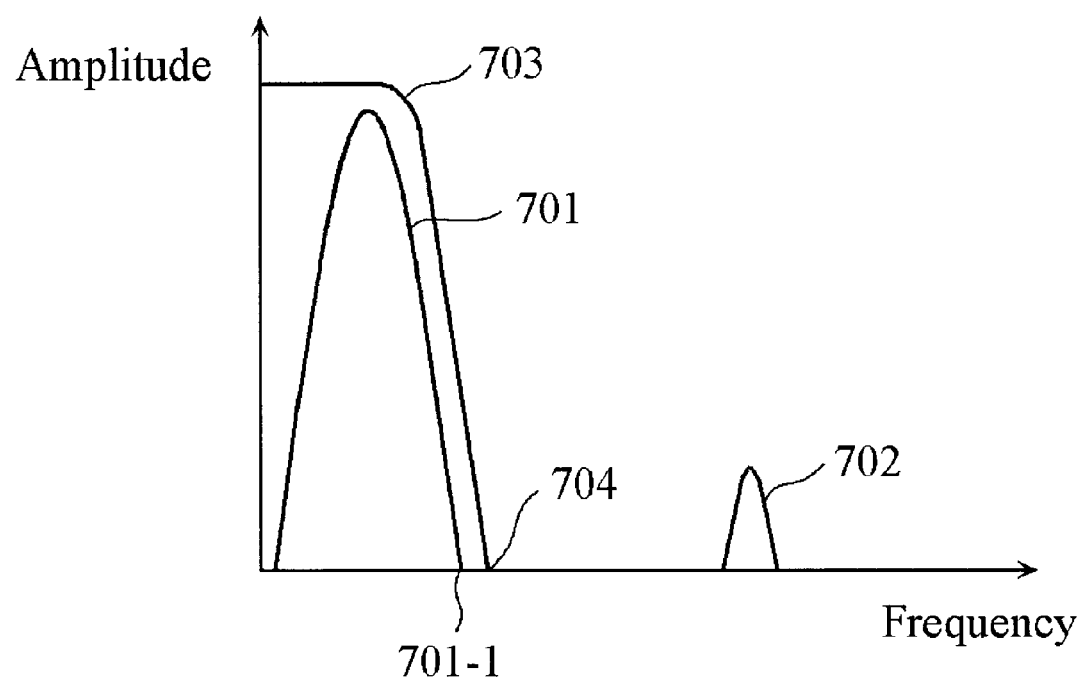
FIG. 5 shows a diagram of a typical low-pass filtering scheme for measuring the velocity component of tissue within the human body.
Figure 6:
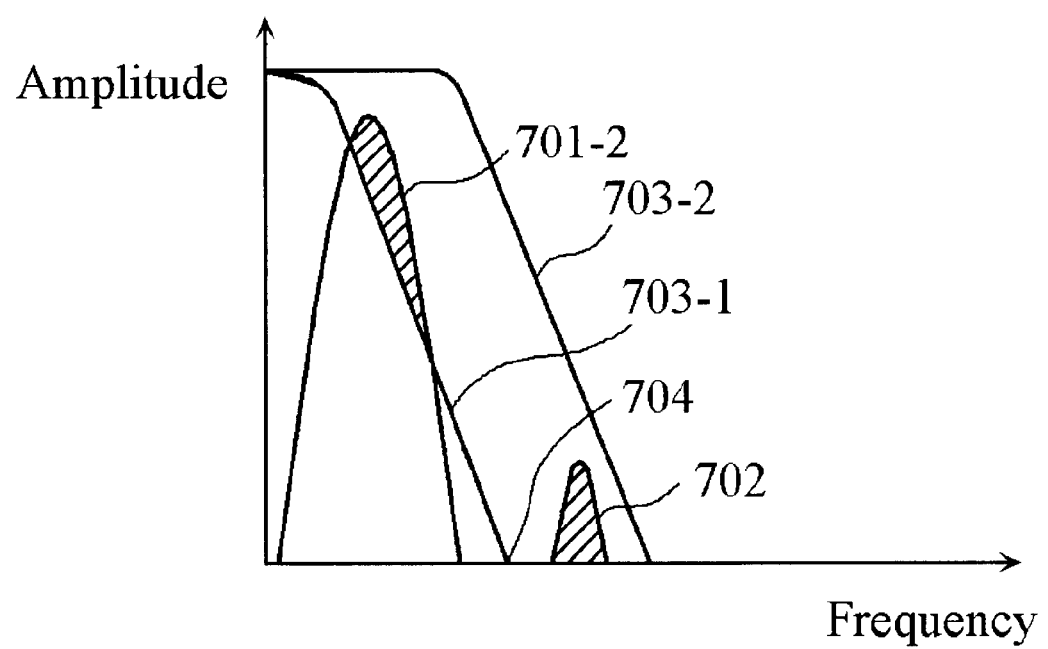
FIG. 6 shows a diagram of a method for designing a cut-off frequency that discriminates the velocity component of tissue from that of blood flow by using the typical low-pass filtering scheme in a conventional ultrasound diagnostic apparatus.
Figure 7:
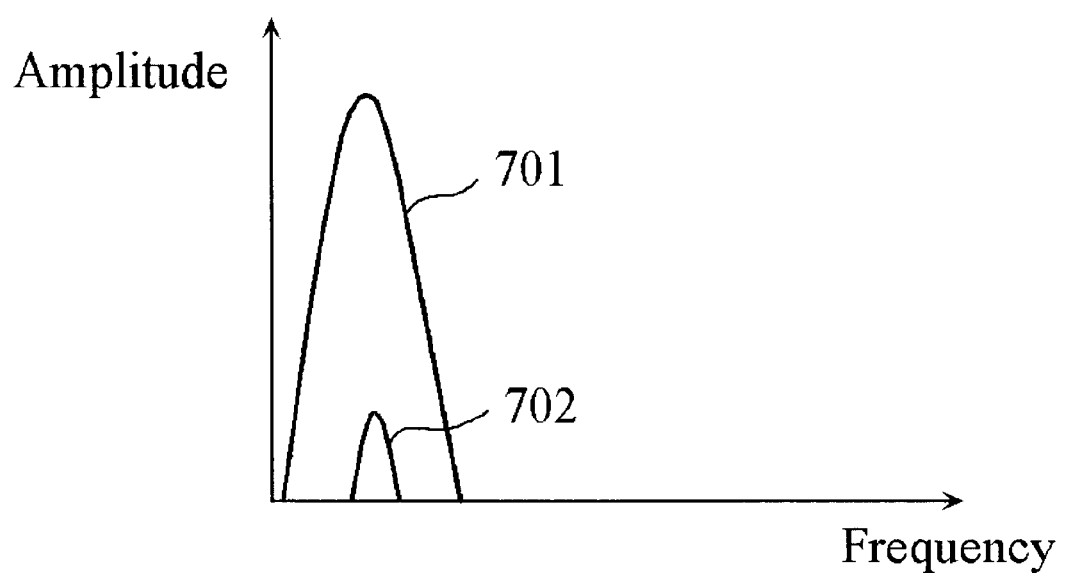
FIG. 7 shows a diagram of the velocity component of blood flow contained in the velocity component of tissue due to aliasing.
Figure 8:
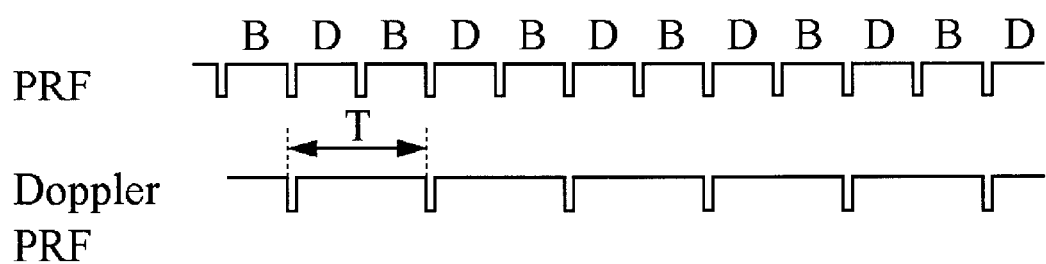
FIG. 8 shows a timing sequence in a typical brightness/Doppler (B/D) simultaneous mode.
Figure 9:
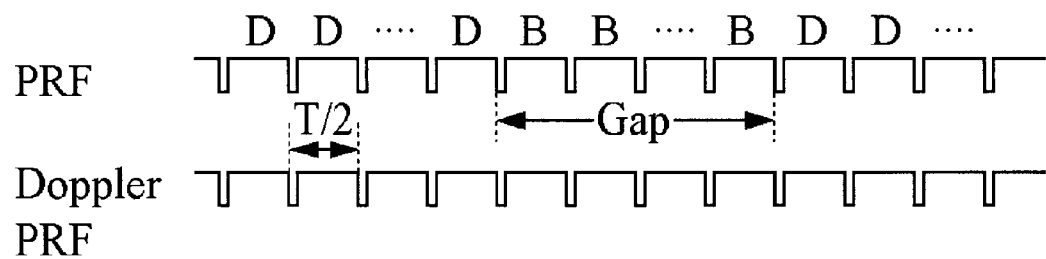
FIG. 9 shows a timing sequence in a gap filling mode.
Figure 10A:
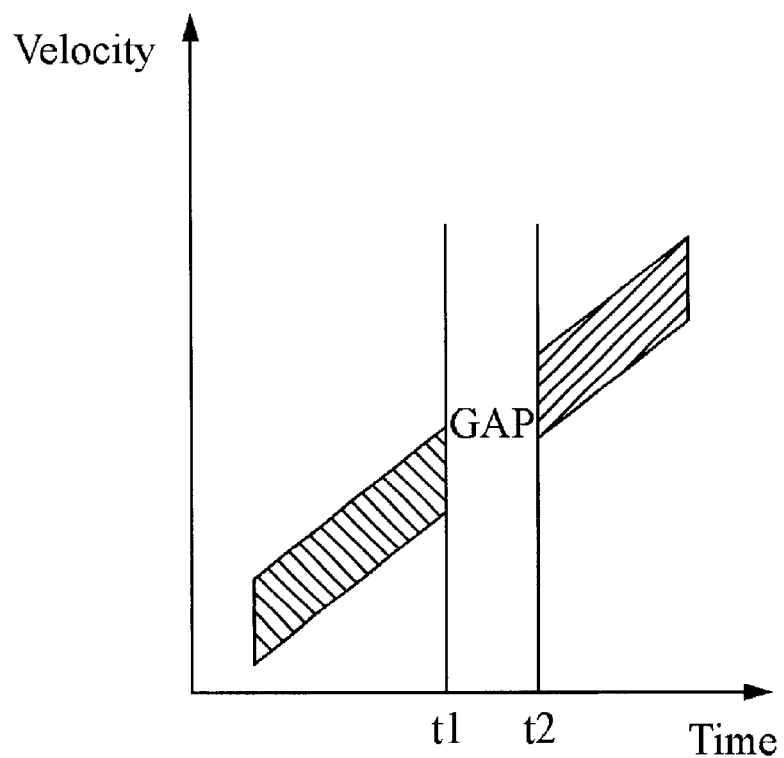
FIGS. 10A and 10B show views explaining the principle of a spectrum gap filling.
Figure 10B:
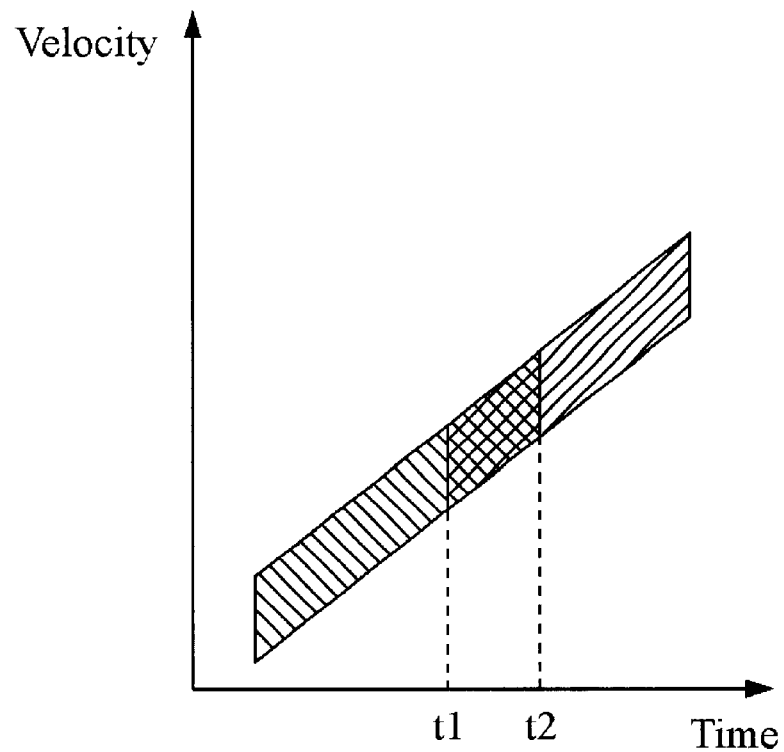
Figure 11:
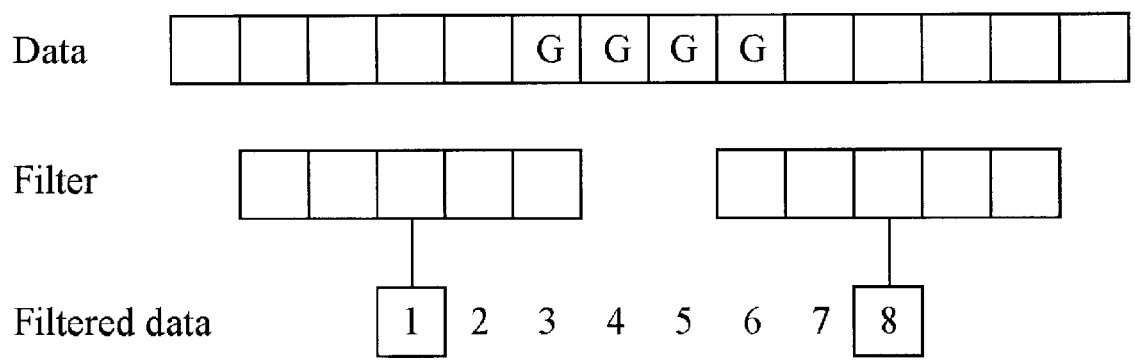
FIG. 11 shows a relationship between the gap and the order of the filter in the gap filling mode.
Figure 12:
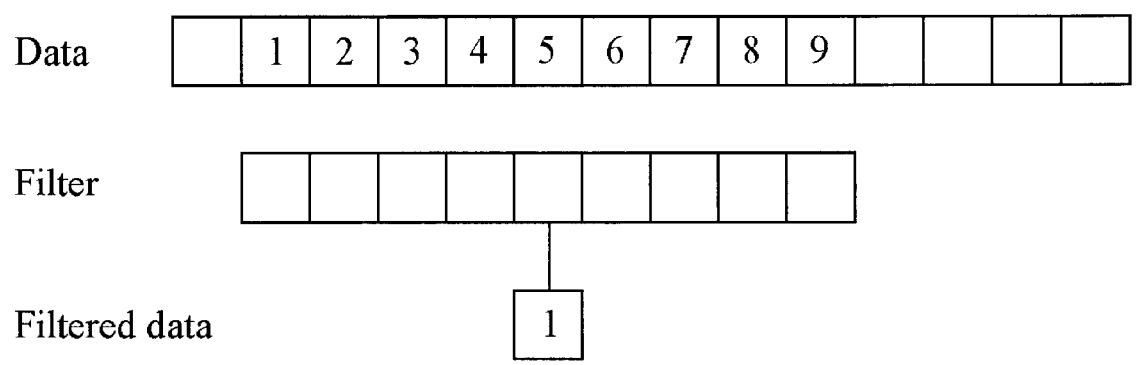
FIG. 12 shows the increase in delay intervals as the order of the filter increases.
Figure 13:
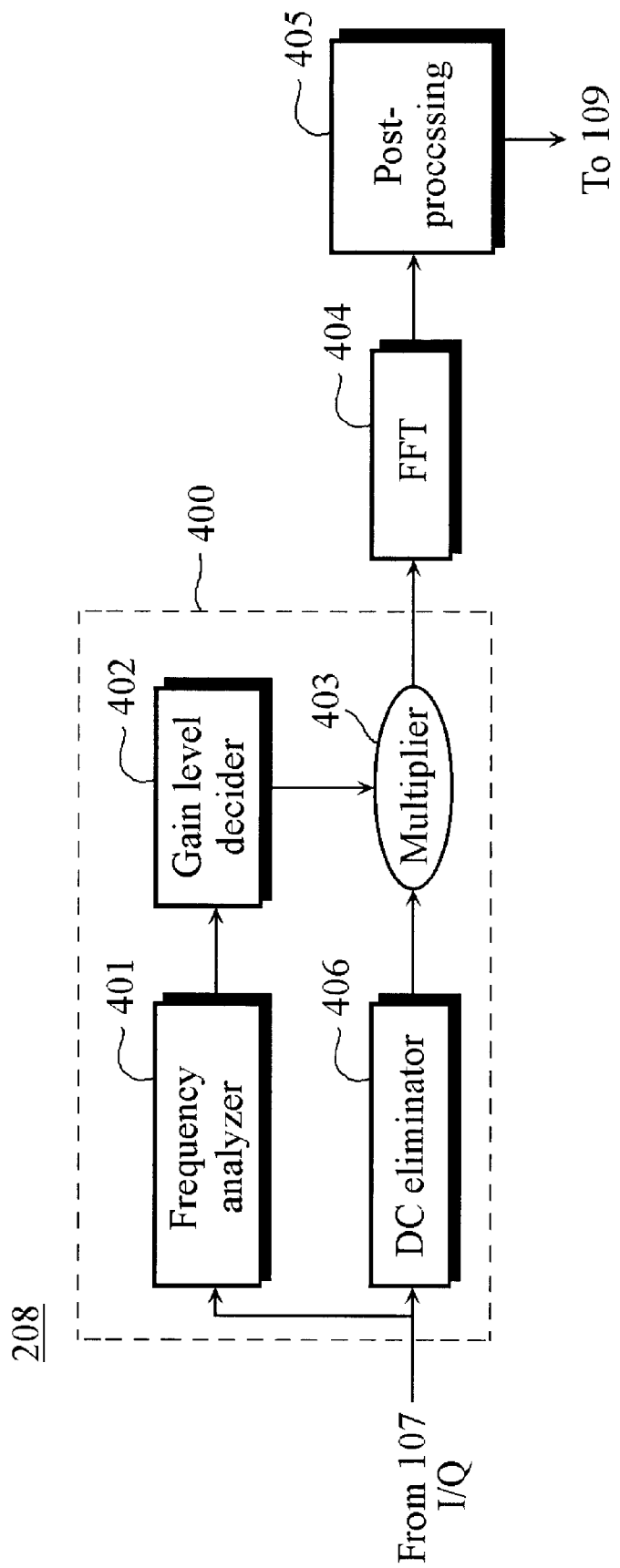
FIG. 13 shows a block diagram of a digital signal processor for measuring the velocity of tissue within the human body in accordance with the present invention.

Referring to FIG. 13, which shows a block diagram of a digital signal processor for measuring the velocity of tissue within a human body in accordance with the present invention, for simplicity, elements of an ultrasound diagnostic apparatus in accordance with the present invention that are identical to those of a conventional ultrasound diagnostic apparatus shown in FIG. 2 are omitted except for digital signal processor 208. As shown in FIG. 13, digital signal processor 208 comprises detecting unit 400 for detecting the velocity of tissue within the human body (instead of clutter filtering unit 301 shown in FIG. 3), fast Fourier transform (FFT) unit 404, and post-processing unit 405. Detecting unit 400 includes frequency analyzer 401, gain level decider 402, multiplier 403, and direct-current (DC) eliminator 406 for separating and measuring the velocity component of tissue in the sampled data from quadrature demodulator 107 shown in FIG. 2.

For example, a number of the sampled data is 2N. Detecting unit 400 separates the velocity component of blood flow among the sampled data, i.e., I/Q data, from quadrature demodulator 107 and effectively eliminates it, to thereby output the velocity component of tissue within the human body.

Figure 14:
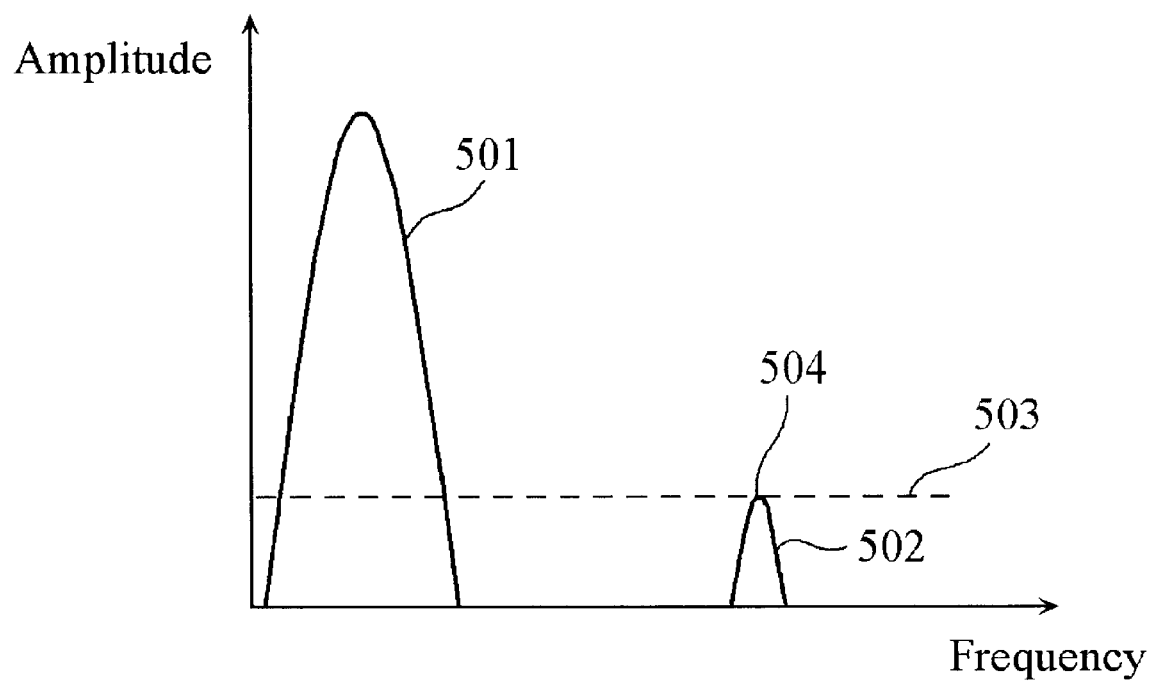
FIG. 14 shows a gain level determined according to a maximum of the velocity component of blood flow, as well as the distribution of the velocity component of tissue and blood flow in a frequency domain of echo signals in accordance with the present invention.

The sampled data (i.e., echo signals reflected from the target object) from quadrature demodulator 107 contains the velocity component of tissue 501 in a low frequency domain and the velocity component of blood flow 502 in a high frequency domain, as shown in the frequency distribution of FIG. 14. The sampled data is simultaneously inputted to DC eliminator 406 and frequency analyzer 401. Frequency analyzer 401 includes a high-pass filter for separating the velocity component of blood flow 502 from the high frequency domain so that inputting the sampled data to frequency analyzer 401 separates the domain representing the velocity component of blood flow. After the sampled data passes the high-pass filter, the velocity component of tissue 501 is eliminated so that only the velocity component of blood flow 502 remains in the sampled data. An FFT unit (not shown) of frequency analyzer 401 performs FFT on the filtered data to produce frequency distribution data for the velocity component of blood flow 502.

Frequency analyzer 401 produces maximum value (i.e., a peak) 504 out of the frequency distribution data for the velocity component of blood flow 502. To effectively produce maximum value 504, a mean time is defined, e.g., a certain period of heartbeats. For example, since the velocity component of blood flow in a cardiac valve is periodically repeated in sync with the heartbeat, producing a maximum value of the velocity component from the velocity component of blood flow during a period of the heartbeat, rather than from the velocity component of blood flow during an arbitrary period is preferable.

Gain level decider 402 decides a gain level suitable for effectively eliminating the velocity component of blood flow depending on the maximum value of the velocity component of blood flow produced as described above. That is, if the maximum value is "A," then the gain level is set to a value capable of making the maximum value "A" equal to zero. For example, if multiplying the maximum value "A" by 0.03 makes "A" equal to zero, then the gain level used in multiplier 403, which is connected to gain level decider 402, is set as 0.03. In a similar manner, if a maximum value were two times "A," then the gain level decider 402 sets 0.015 as a gain level used in multiplier 403.

DC eliminator 406 eliminates the DC component of the sampled data from quardature demodulator 107 shown in FIG. 2 to provide to multiplier 403. Multiplier 403 then multiplies the DC-component-eliminated sampled data from DC eliminator 406 by a gain level 503 decided by gain level decider 402, as shown in FIG. 14, thereby eliminating the velocity component of blood flow 502 from the sampled data containing the velocity component of tissue. As a result, detecting unit 400 may separate and measure the velocity component of tissue out of the sampled data from quadrature demodulator 107.

Thereafter, the velocity component of tissue measured by detecting unit 400 is inputted to FFT unit 404. FFT unit 404 performs FFT on the sampled data containing the velocity component of tissue to produce frequency distribution data containing 2N number of frequency component. The frequency distribution data corresponds to a velocity distribution spectrum of the velocity component of tissue within the human body. Post-processing unit 405 processes the frequency distribution data, by using known log compression and base line shifting techniques, in order to obtain an improved diagnostic image. Since the amplitude of the velocity component of tissue, which is originally obtained, is reduced by the gain level multiplied in multiplier 403, in order to compensate for the reduction of the amplitude, post-processing unit 405 additionally multiplies a predetermined gain level to the velocity component of tissue. The processed frequency distribution data, i.e., the velocity distribution spectrum representative of the velocity component of tissue, from post-processing unit 405, is inputted to display 109 shown in FIG. 2.

As described above, the ultrasound diagnostic apparatus according to the present invention multiplies a value of less than 1, e.g., 0.04 or 0.03, to echo signals that contain a velocity component of tissue and blood flow, thereby effectively eliminating the velocity component of blood flow having a value relatively less than that of the velocity component of tissue.

Figure 15:
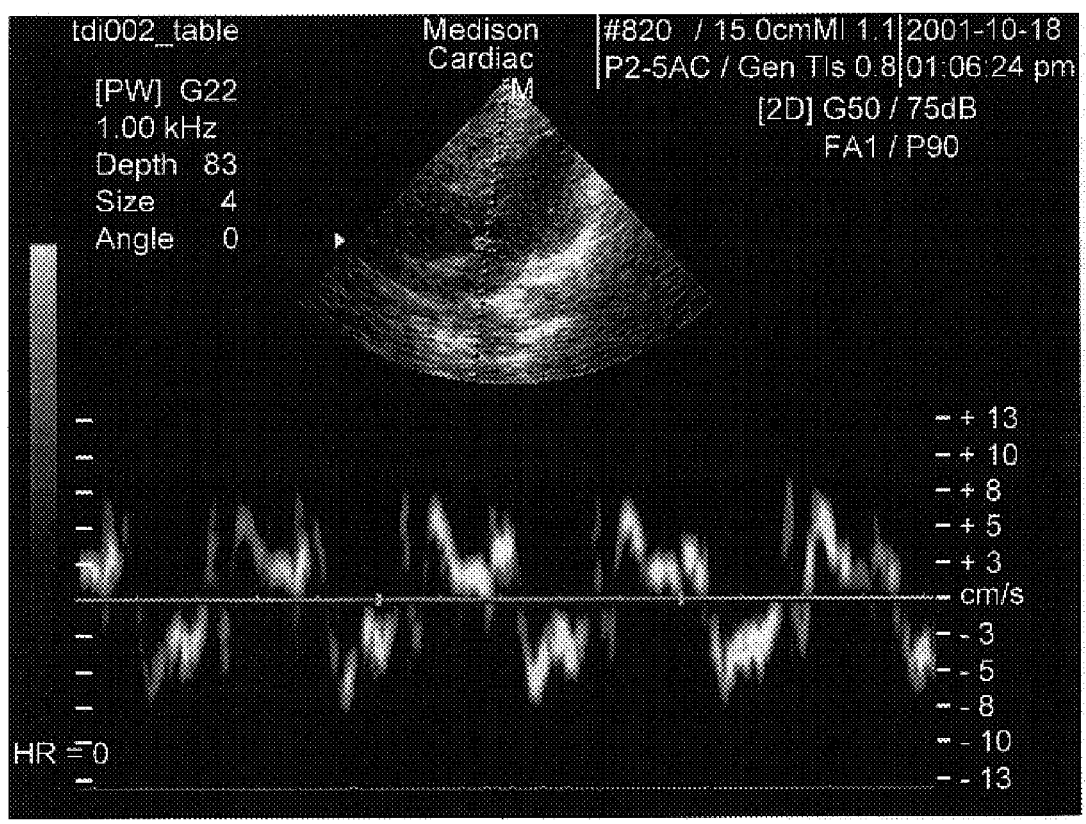
FIG. 15 shows an example of a picture representing the velocity of blood in a pericardium or a cardiac valve measured by an ultrasound diagnostic apparatus in accordance with the present invention.

Referring to FIG. 15, which shows an example of a picture representing the velocity of blood flow in a pericardium or a cardiac valve as measured by an ultrasound diagnostic apparatus in accordance with the present invention, the ultrasound diagnostic apparatus has the following advantages.

First, in order to measure the velocity component of the tissue, the ultrasound diagnostic apparatus takes advantage of a virtual low-pass filter by using the amplitude difference between the velocity component of tissue and blood flow (instead of a low-pass filter in the prior art) and employing a gain level multiplication method capable of eliminating the velocity component of blood flow. As a result, the ultrasound diagnostic apparatus sets a gain level independent of the variation of the velocity component of tissue within the human body. Thus, unlike the prior art, changing the cut-off frequency is not necessary because a low-pass filter is not employed in the ultrasound diagnostic apparatus according to the present invention.

Second, where the ultrasound diagnostic apparatus measures velocity and power components, distortion is limited to the amplitude component, since aliasing is eliminated by moving the velocity component of blood flow through the application of an appropriate gain level. Distortion of the amplitude component may be fixed in the afore-mentioned post-processing procedure to entirely block the distortion of the amplitude of the velocity component of tissue. As a result, the ultrasound diagnostic apparatus according to the present invention avoids calculation error due to aliasing and thereby increases the reliability of measured data.

Third, since the ultrasound diagnostic apparatus does not employ a low-pass filter to measure the velocity component of tissue within the human body, delays due to the low-pass filter, as much as an order of filter $(N-1)/2$, do not occur. The real-time processing capability is increased and the data sections to be filled are reduced by as much as the filter order in the gap filling mode. As a result, the calculation process in the ultrasound diagnostic apparatus according to the present invention is simpler than in the prior art.

While the present invention has been shown and described with respect to the particular embodiments, those skilled in the art will recognize that many changes and modifications may be made without departing from the spirit and scope of the invention as defined in the appended claims.

What is claimed is:

1. An ultrasound diagnostic apparatus for measuring a velocity component of tissue and blood flow within a human body, comprising:

a sample data generator for generating sample data by transmitting ultrasound signals to and sampling echo signals reflected from the human body;

generating means for generating frequency distribution data containing the velocity component of tissue and blood flow by processing the sample data, wherein the frequency distribution data contains a plurality of frequency components, each of which has a power level;

detecting means for extracting the frequency distribution data corresponding to the velocity component of tissue flow from the frequency distribution data, by using a maximum value of the velocity component of blood flow; and a display coupled to the detecting means for displaying the extracted frequency distribution data, wherein the detecting means further comprises:

input means for inputting the frequency distribution data containing the velocity component of tissue and blood flow;

eliminating means for eliminating a direct-current (DC) component of the frequency distribution data;

extracting means for extracting the velocity component of blood flow from the frequency distribution data;

determining means for determining a maximum value of the extracted velocity component of blood flow;

a gain level decider responsive to the determined maximum value for deciding a gain level; and a multiplier for multiplying the frequency distribution data by the decided gain level.

2. The apparatus of claim 1, wherein the gain level is determined such that multiplying the frequency distribution data by the decided gain level makes the maximum value of the extracted velocity component of blood flow equal to zero.

3. The apparatus of claim 1, wherein the maximum value is determined based on a mean value of the velocity component of blood flow during a predetermined time.

4. The apparatus of claim 1, wherein the detecting means further comprises means for multiplying the extracted frequency distribution data by the decided gain level to compensate for amplitude loss of the velocity component of tissue.

5. A method for measuring a velocity component of tissue and blood flow within a human body, comprising the steps of:

generating sample data by transmitting ultrasound signals to and sampling echo signals reflected from the human body;

generating frequency distribution data containing the velocity component of tissue and blood flow by processing the sample data, wherein the frequency distribution data contains a plurality of frequency components, each of which has a power level;

extracting the frequency distribution data corresponding to the velocity component of tissue flow from the frequency distribution data, by using a maximum value of the velocity component of blood flow; and displaying the extracted frequency distribution data, wherein the extracting step further comprises the steps of:

receiving the frequency distribution data containing the velocity component of tissue and blood flow;

eliminating a direct-current (DC) component from the frequency distribution data;

extracting the velocity component of blood flow from the frequency distribution data;

determining a maximum value of the extracted velocity component of blood flow;

deciding a gain level by using said determined maximum value; and multiplying the frequency distribution data by the decided gain level.

6. The method of claim 5, wherein the gain level is determined such that multiplying the frequency distribution data by the decided gain level makes the maximum value of the extracted velocity component of blood flow equal to zero.

7. The method of claim 5, wherein the maximum value is determined based on a mean value of the velocity component of blood flow during a predetermined time.

8. The method of claim 5, wherein the extracting step further comprises multiplying the extracted frequency distribution data by the decided gain level to compensate for amplitude loss of the velocity component of tissue.

* * * * *